(12) United States Patent
Shapiro

(10) Patent No.: US 6,995,839 B1
(45) Date of Patent: Feb. 7, 2006

(54) AUTOMATED RAMAN SCANNER FOR DOCUMENTS AND MATERIALS

(76) Inventor: Frederick W. Shapiro, 3504 Nodding Pine Ct., Fairfax, VA (US) 22033

( * ) Notice: Subject to any disclaimer, the term of this patent is extended or adjusted under 35 U.S.C. 154(b) by 145 days.

(21) Appl. No.: 10/681,039

(22) Filed: Oct. 8, 2003

Related U.S. Application Data

(60) Provisional application No. 60/416,853, filed on Oct. 8, 2002.

(51) Int. Cl.
  *G01J 3/44*   (2006.01)
  *G01N 21/65*  (2006.01)
  *G06K 9/74*   (2006.01)

(52) U.S. Cl. .......................................... 356/301; 356/71

(58) Field of Classification Search ................ 356/301, 356/71; 355/122, 99, 84; 399/377, 380, 399/17, 9
See application file for complete search history.

(56) References Cited

U.S. PATENT DOCUMENTS

| | | | | |
|---|---|---|---|---|
| 5,563,685 A | * | 10/1996 | Onthank | 355/75 |
| 5,818,047 A | * | 10/1998 | Chaney et al. | 250/341.8 |
| 6,122,481 A | * | 9/2000 | Rusnack | 399/380 |
| 6,249,339 B1 | * | 6/2001 | Jung et al. | 356/71 |
| 6,275,285 B1 | * | 8/2001 | Nottke et al. | 356/71 |
| 6,744,500 B2 | * | 6/2004 | Bradbury et al. | 356/301 |

FOREIGN PATENT DOCUMENTS

WO      WO 9111703 A1 *   8/1991

* cited by examiner

Primary Examiner—Gregory J. Toatley, Jr.
Assistant Examiner—Sarah J. Chisdes
(74) Attorney, Agent, or Firm—Michael P Fortkort; Michael P Fortkort PC

(57) ABSTRACT

A scanner employs Raman spectroscopy for on site automated materials authenticity verification and identification. A technology developed so that operators with little or no technical expertise can perform on site fast nondestructive materials analyses. Automated generation of Raman signatures, and subsequent correlation to spectral fingerprints of known materials provides an ideal means for documentation verification or materials identification in settings like airport ticket counters, U.S. Customs gates, law enforcement vehicles and business offices (such as a physician's examination room). Computer controlled moveable optics provides for a scanning capability to automatically and precisely analyze several locations on a sample. The Raman scanner also provides for on site materials analysis requiring a high level of technical expertise to be done by transmission of the spectral data to a remote location via modem or wireless communications using a transmitter and receiver.

28 Claims, 5 Drawing Sheets

Raman Scanner Top View

Raman Scanner Internal View Standard Operation Mode

Raman Scanner Internal View Optical Probe Operation Mode

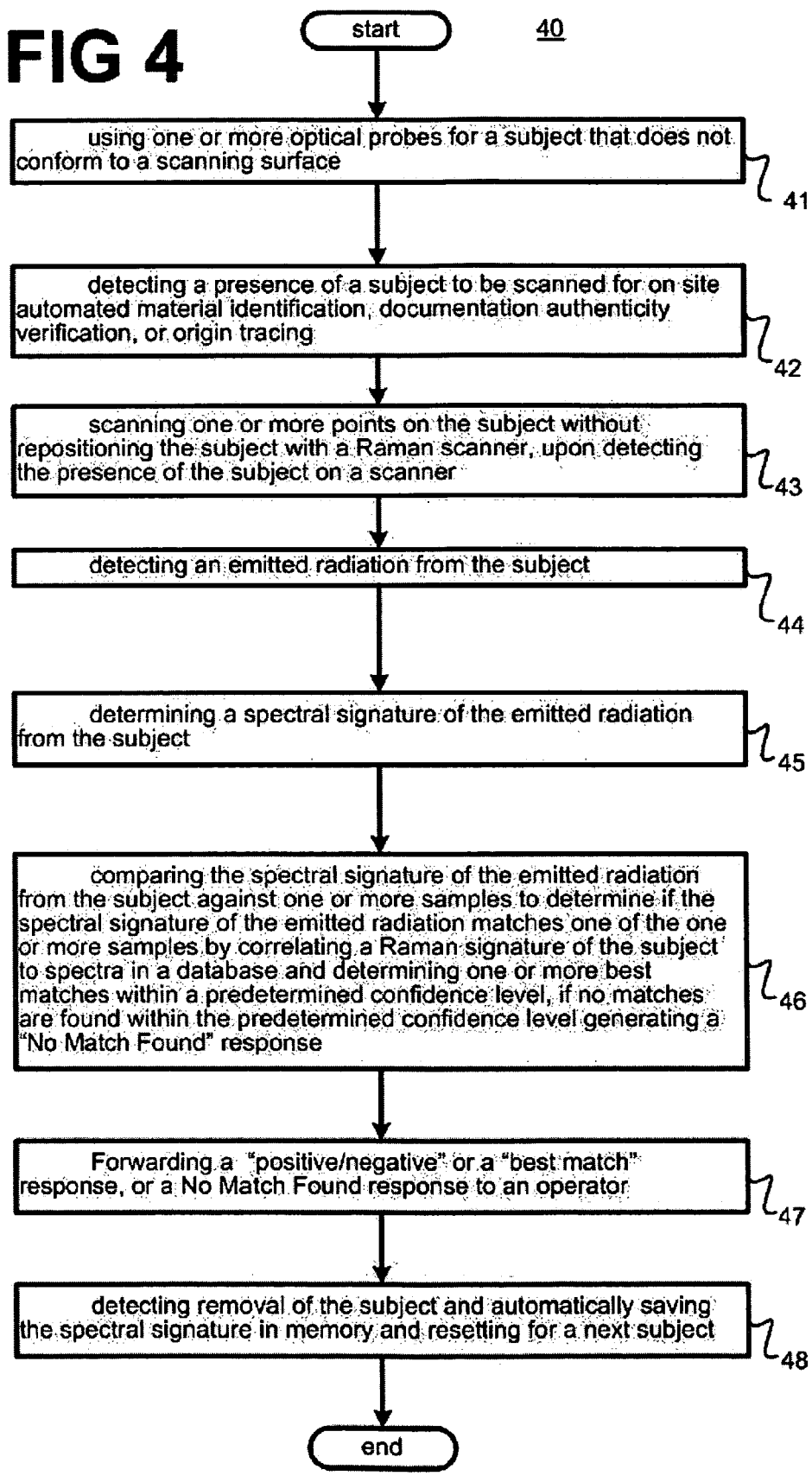

FIG 5 start 50

↓ using one or more forms to accurately position the subject on a scanner surface — 51

↓ using one or more optical probes for a subject that does not conform to a scanning surface — 52

↓ placing an adaptor on the subject that conforms to the subject surface profile to ensure that no ambient light contaminates a subject spectral signature — 53

↓ filtering out erroneous spectral features in a sample signature — 54

↓ detecting a presence of a subject to be scanned for on site automated material identification, documentation authenticity verification, or origin tracing — 55

↓ automatically generating a Raman spectra of one or more points on the subject — 56

↓ transmitting the spectral signature over a communications link for analysis — 57

↓ comparing the spectral signature of the emitted radiation from the subject against one or more samples to determine if the spectral signature of the emitted radiation matches one of the one or more samples by correlating a Raman signature of the subject to spectra in a database and determining one or more best matches within a predetermined confidence level, if no matches are found within the predetermined confidence level generating a "No Match Found" response, and forwarding the one or more best matches or the "No Match Found" response to the operator — 58

↓ end

AUTOMATED RAMAN SCANNER FOR DOCUMENTS AND MATERIALS

STATEMENT OF RELATED APPLICATION

This application claims the benefit of priority to U.S. Provisional Patent Application No. 60/416,853, filed Oct. 8, 2002 by the same inventor, and entitled "Automated Raman Scanner."

FIELD OF THE INVENTION

The present invention is directed to methods and apparatuses for automated non-invasive examination, and more particularly to a method and apparatus for non-invasive examination using optical scanning and Raman spectroscopy.

BACKGROUND

Individuals and organizations seek to transfer materials and mis-identified people through a country's borders without detection by the border officials. Thus, a need exists for simple, rapid detection of contraband materials and forged documents.

The present invention is therefore directed to the problem of developing a method and apparatus for scanning objects and documents in a quick yet effective manner, which can be accomplished using a portable device.

SUMMARY OF THE INVENTION

The present invention solves these and other problems by providing a portable, automatic Raman scanner that compares a spectral signature of a sample against a database of known spectral samples to identify suspicious materials or documents.

According to a first aspect of the present invention, an apparatus for performing on-site automatic, nondestructive materials analysis on a subject using Raman spectroscopy includes a Raman scanner, a database and a processor. The Raman scanner employs one or more laser light sources that illuminate the subject via an optical path. The Raman scanner includes a highly sensitive charge coupled device camera to collect emitted radiation. The database stores spectral fingerprints of known samples. The scanner automatically generates a spectral signature from the subject and the processor compares the generated spectral signature to the known samples in the database.

According to another aspect of the present invention, the processor may generate a "positive/negative" or a "best match" response based on a statistical algorithm and forward the result to an operator.

According to still another aspect of the present invention, the apparatus may include a memory in which the processor can save the spectral signature, thereby enabling the processor to reset for a next sample.

According to another aspect of the present invention, one or more points on the subject can be scanned without physically repositioning the subject.

According to yet another aspect of the present invention, the apparatus may also include one or more optical probes for scanning a particular subject that does not conform to a scanning surface.

According to still another aspect of the present invention, the apparatus may also include computer readable media having encoded thereon instructions that cause the processor to automate capture and correlation of a Raman signature of the subject to spectra in the database and determine a best match or matches within a designated confidence level, wherein if no matches are found within the designated confidence level a "No Match Found" response may be generated and forwarded to the operator.

According to a further aspect of the present invention, the apparatus may also include computer readable media having encoded thereon spectral-correlation software to enable the apparatus to provide: capability to automatically trace a material to its origin using a database of known Raman signatures; on site documentation authenticity verification; or on site automated material identification or verification.

According to still another aspect of the present invention, the apparatus may also include computer controlled moveable optics to provide materials analysis of more than one point along a subject without physically moving the subject. In this case, the processor may automatically generate Raman spectra of one or more points on the subject and correlate them against spectra in the database of known materials.

According to yet another aspect of the present invention, the processor may automatically detect a presence of the subject on a scanner surface and initiate generation of a spectral signature. In this case, the processor may also sense removal of the subject and then store a spectral signature and automatically reset for a next subject.

According to another aspect of the present invention, the apparatus may include a battery to power it, thereby making the apparatus portable.

According to still another aspect of the present invention, the apparatus may include a communications device to transmit the results to a central location.

According to another aspect of the present invention, the Raman scanner may include one or more optical probes that utilize conjugated optics for subjects that are inaccessible or do not conform to the scanner surface.

According to yet another aspect of the present invention, the scanner may include one or more forms for accurate positioning of a subject on the scanner surface.

According to another aspect of the present invention, the scanner may include more than one source laser.

According to a further aspect of the present invention, the scanner may include an adaptor that conforms to a subject surface profile to insure that no ambient light contaminates a subject spectral signature.

According to still another aspect of the present invention, the apparatus may include computer readable media having encoded thereon software to filter out erroneous spectral features in a sample signature.

According to another aspect of the present invention, a method for analyzing a subject includes scanning the subject with a Raman scanner, detecting an emitted radiation from the subject, determining a spectral signature of the emitted radiation from the subject, and comparing the spectral signature of the emitted radiation from the subject against one or more samples to determine if the spectral signature of the emitted radiation matches one of the one or more samples.

According to another aspect of the present invention, a "positive/negative" or a "best match" response may be generated and forwarded to an operator.

According another aspect of the present invention, a presence of the subject may be detected thereby automatically initiating the scanning upon detecting the presence of the subject. Furthermore, removal of the subject may be detected thereby initiating automatically saving of spectral signature in memory and resetting for a next subject.

According another aspect of the present invention, one or more points on the subject may be scanned without physically repositioning the subject.

According another aspect of the present invention, one or more optical probes may be used for scanning a particular subject that does not conform to a scanning surface.

According another aspect of the present invention, the comparing includes correlating a Raman signature of the subject to spectra in a database and determining one or more best matches within a predetermined confidence level, if no matches are found within the predetermined confidence level generating a "No Match Found" response, and forwarding the one or more best matches or the "No Match Found" response to the operator.

According another aspect of the present invention, on site automated material identification, on site documentation authenticity verification, and tracing of a material to its origin is made possible.

According to another aspect of the present invention, a method for analyzing a subject includes automatically generating a Raman spectra of one or more points on the subject, and comparing the spectral signature of the emitted radiation from the subject against one or more samples to determine if the spectral signature of the emitted radiation matches one of the one or more samples.

According another aspect of the present invention, the spectral signature may be transmitted over a communications link for analysis.

According another aspect of the present invention, one or more forms may be used to accurately position the subject on a scanner surface.

According another aspect of the present invention, an adaptor may be placed on the subject that conforms to the subject surface profile to ensure that no ambient light contaminates a subject spectral signature.

According another aspect of the present invention, erroneous spectral features may be filtered in a sample signature to improve accuracy of the results.

BRIEF DESCRIPTION OF THE DRAWINGS

FIG. 4 depicts an exemplary embodiment of a method for scanning a subject according to another aspect of the present invention.

FIG. 5 depicts an exemplary embodiment of a method for scanning a subject according to another aspect of the present invention.

DETAILED DESCRIPTION

Figure 1:
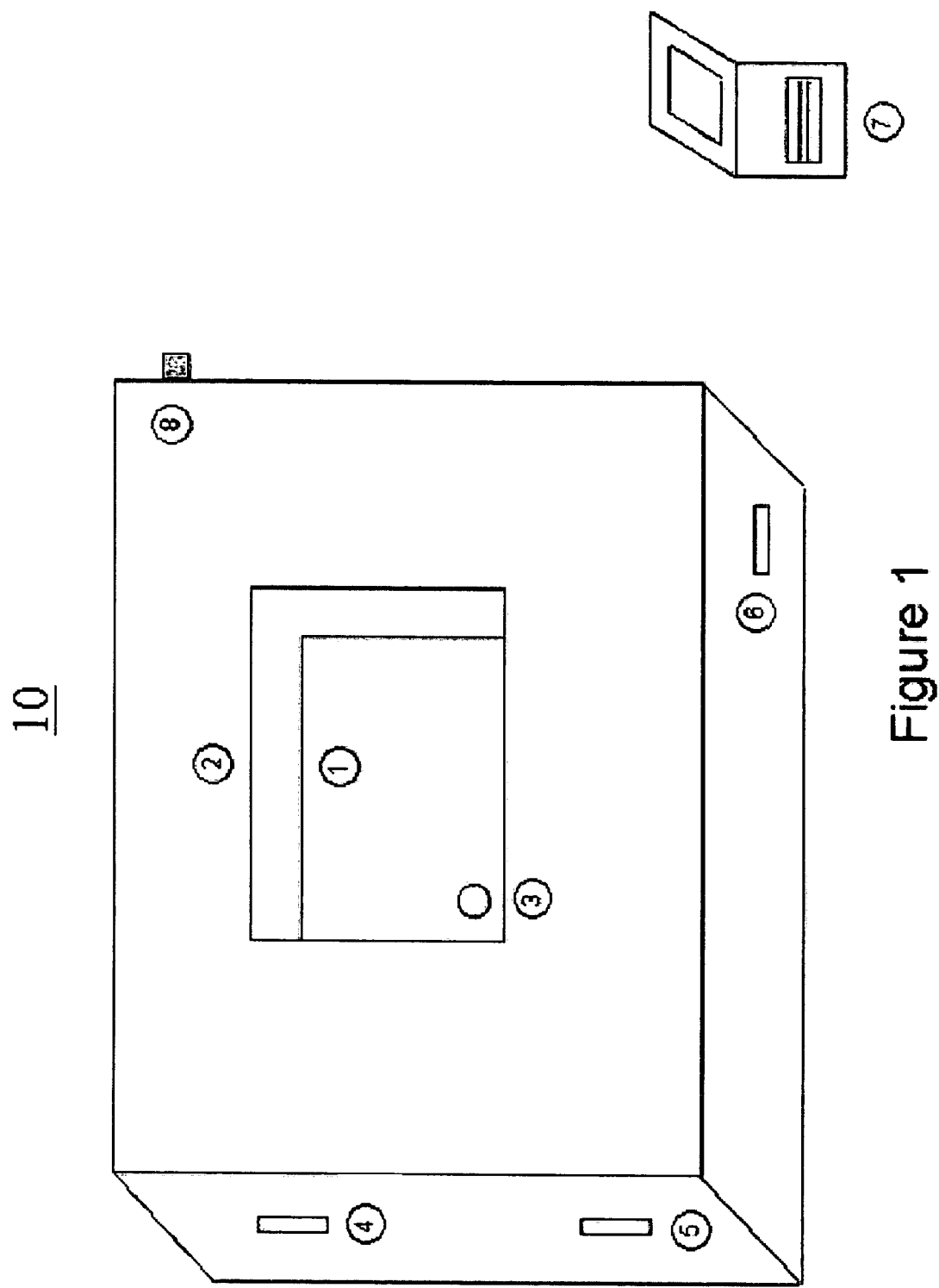
FIG. 1 depicts an exemplary embodiment of a Raman Scanner in a top view according to one aspect of the present invention.

It is worthy to note that any reference herein to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

These embodiments of the present invention address form, fit, and function modifications to conventional Raman spectrographic technology resulting in an automated Raman scanner to be used for on site material identification and verification. Mechanical, optical and software modifications and enhancements are made to conventional Raman spectrographic technology to permit this capability.

The Raman scanner of the present invention enables fast, nondestructive analysis in an automated manner to on-site materials in a non-laboratory environment. The Raman scanner function is automated to be user-friendly and requires very little user training or technical expertise. The Raman scanner is capable of being portable and battery powered. The Raman scanner can accommodate both large and small sized samples.

The form of the scanner provides a surface similar to a bar code scanner to analyze smaller objects. Mechanical forms are included for applications where positioning of the subject is critical to achieve a spectral signature required for accurate identification or verification.

An example of the use of forms includes personal identification verification in an airport environment. To verify the authenticity of a passport or driver's license, it is imperative to scan the appropriate portion or portions of the documentation. A form (e.g., an outline or depression into which the document is placed) ensures proper alignment of the document in the scanner. The document will be placed in the scanner and scanned either automatically or via operator prompt on a laptop computer.

Optical probes are included to analyze large or immobile subjects that do not conform easily to the scanner surface. Conjugated optics are used to collect and guide light into and out of the optical probes. The scanner surface and the optical probes are fitted with adapters that conform to the shape of the subject to prevent ambient light from contributing to the Raman spectrum of the sample.

Optical modifications can be made to suit each particular application. The source laser wavelengths selected can be based on the materials of interest for each individual application. Optics selection is optimized for sample spectra signature strength and scanner design parameters, such as size, weight, and power consumption. The optical path is modified from conventional Raman technology to accommodate a scanner form and function similar to a bar code reader. Raman scanners are adapted to include more than one laser if the application includes multiple distinct sample types requiring more than one source wavelength.

An example of this occurs at a customs gate where both personal identification verification and drug identification are required. A highly sensitive CCD camera is used to detect emitted radiation based on the source laser wavelengths.

Software modifications enable conventional laboratory Raman spectrographic technology to be converted to an on-site automated materials analysis capability. The scanner is employed in conjunction with a laptop or stand-alone computer system. User-friendly software prompts the operator to place the sample in the scanner. The scanner detects that a sample is in place and automatically scans the subject.

Software enhancements permit automatic selection of a number and location of points to be scanned on each subject type. Data acquisition software enables a Raman spectral signature to be automatically generated for the subject. The resulting Raman spectral signature may be automatically compared to control spectra in a database for authenticity verification or material identification.

A "positive/negative" response is generated based on a high confidence level and provided to the operator for authenticity verification, such as in passport validation. A "best match" list may be provided to the operator along with degree of confidence for material identification, such as in drug analysis. If the match is below a preset confidence threshold, the computer may post a "No Match Found" result.

The scanner senses removal of the sample and automatically resets for a next subject. All sample signatures can be automatically catalogued and saved.

Optionally, the embodiment can include a communications device via which Raman signatures of negative responses may be transmitted to a remote location for further analysis by trained operators. This communications device can include a modem or wireless communications device. Identification of a manufacturer origin of the sample may then be achieved by comparison of the subject Raman spectral signature to databases of known samples.

The form of the Raman scanner is modified to exhibit a minimal footprint to fit easily in a relatively small space. The type of setting in which the scanner will be used may require limited space and ease of accessibility such as an airport ticket counter, U.S. Customs gate, law enforcement vehicle, or a medical office.

FIG. 1 shows a top view of an exemplary embodiment 10 of a Raman Scanner according to a first aspect of the present invention. The scanner surface 1 is composed of a transparent material that contributes no spectral features in the fingerprint region of the spectrum. Many glass materials would be suitable. Form 2 depicted in FIG. 1 is a form designed for each subject. The purpose of the form is to insure accurate alignment of the subject on the scanner surface 1. The form 2 may take alternate sizes and shapes depending on the particular application and the positioning accuracy required. An optical sensor 3 is used to alert the system that a subject has been placed on the scanning surface 1 and is ready to be analyzed. The optical sensor 3 initiates the automated analysis process. Ports 4, 5, 6 are interfaces to interface the scanner laser, CCD camera, and optics-positioning controller, respectively, with a laptop or standalone computer 7. Interface port 8 is an interface port for optical probes used to analyze large or immobile subjects that are unsuitable for the scanning surface 1.

Figure 2:
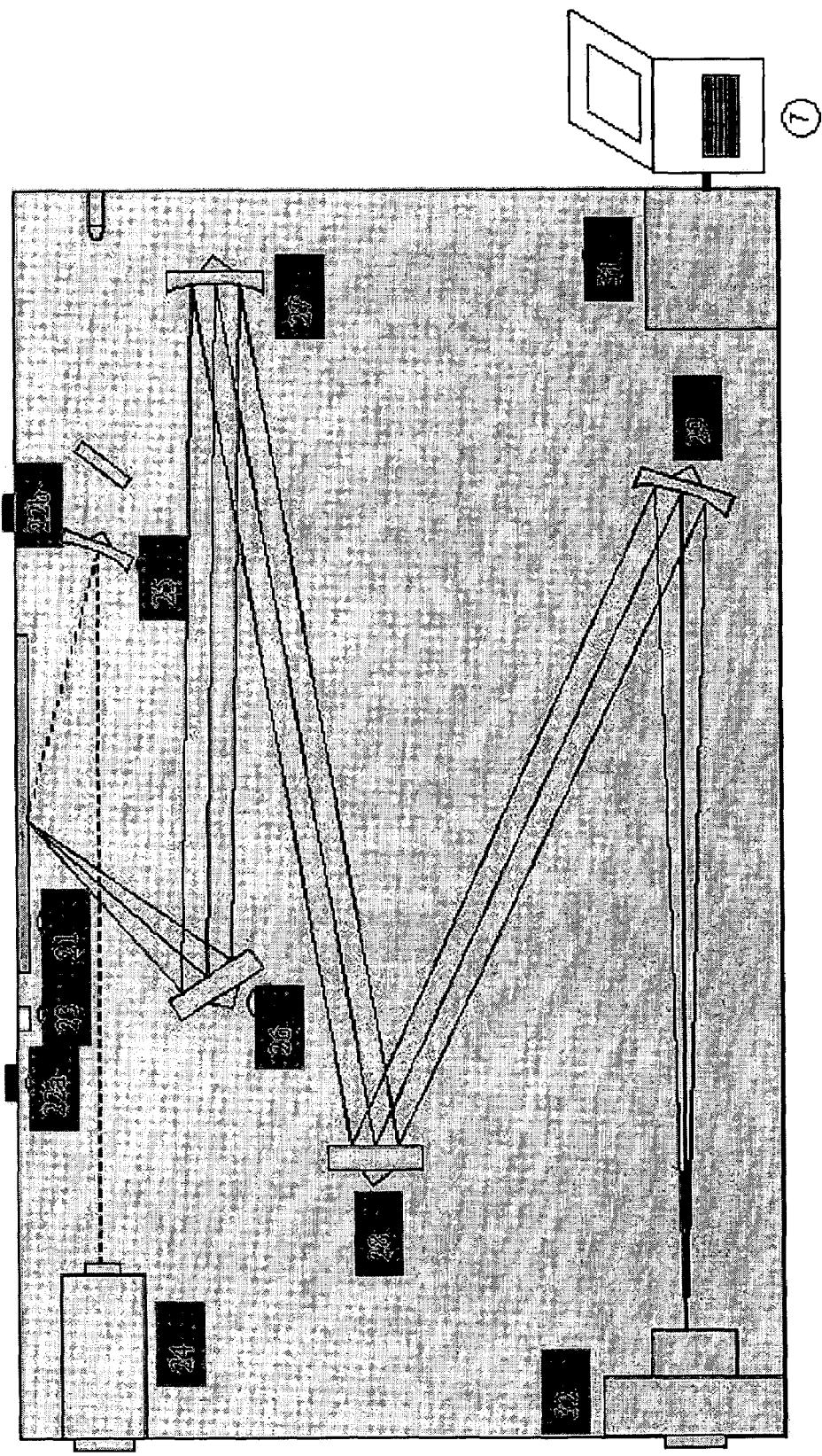
FIG. 2 depicts an internal view of an exemplary embodiment of a Raman Scanner Standard Operation Mode according to another aspect of the present invention.

FIG. 2 depicts an exemplary embodiment 20 of the scanner operation. Computer controlled moveable optics are incorporated to permit scanning of more than one point without the need to physically relocate the subject, if required, for accurate identification or verification. A subject such as a passport is placed on the scanner surface 21. The edges 22a, 22b of the form position the subject so that the correct portion of the material is scanned. The sensor 23 detects presence of a subject and initiates the materials analysis. Laser source 24 has a wavelength and intensity selected for the particular application. The laser light is transmitted to a moveable mirror 25, which then redirects the light to the correct location on the scanner surface 21. The rotating feature of the mirror 25 permits the laser light from laser source 24 to illuminate the surface of the subject in more than one location if desired. Raman radiation scattered back through the scanner surface 21 from the test subject is captured by the moveable optics 26, 27, 28 and 29 and is focused on a CCD camera 32. Optics 26, 27 and 29 are reflecting mirrors used to capture and focus the emitted radiation from the subject. Optics 28 is a grating selected for the particular application to disperse the shifted wavelengths of emitted radiation. Controller 31 is used to drive the moveable optics.

The controller 31 is commanded by the laptop or standalone computer system 7. Spectral data collected by the CCD camera 32 is transmitted to the laptop computer 7 and analyzed. The laptop 7 automatically searches pre-selected spectral databases and uses correlation software to determine the "best matches" within a specified confidence level if any exist. The result is automatically transmitted to the operator. The optical sensor 23 senses the removal of the test subject and automatically resets the scanner for the next subject. The spectral fingerprint(s) of the test subject is automatically saved and catalogued.

Figure 3:
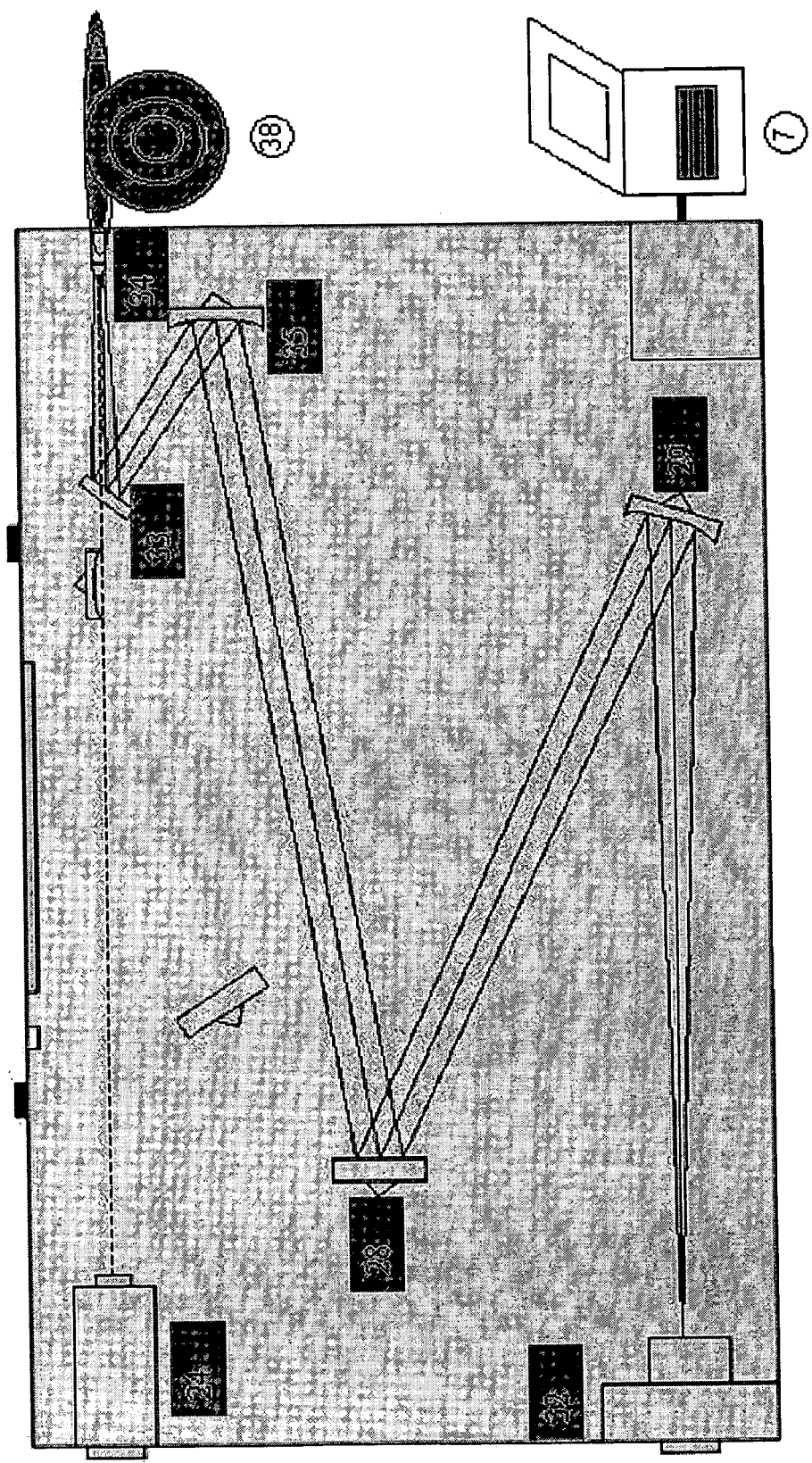
FIG. 3 depicts an internal view of an exemplary embodiment of the Raman Scanner Optical Probe Operation Mode according to yet another aspect of the present invention.

Optical probes 38 may be included to analyze large or immobile subjects that will not conform easily to the scanner surface. FIG. 3 depicts an exemplary embodiment 30 of an internal view of the scanner operation using the optical probes. The source laser 24 has a wavelength and intensity selected for the particular application. The laser light is focused on the optical probe port 34, which is then transmitted to the test subject via conjugated optics and optical probes 38. The optical probes 38 will be made of a graded index material selected for low loss over the operating wavelength range and will contribute no spectral features into the subject Raman signature. Scattered Raman radiation is captured via conjugated optics and transmitted back through the probes to the optics 33, 35, 28 and 29 and focused on a CCD camera 32. Optics 33, 35 and 29 are reflecting mirrors used to capture and focus the emitted radiation. Optics 28 is a grating selected for the particular application to disperse the different wavelengths of emitted radiation.

Spectral data collected by the CCD camera 32 is transmitted to the laptop computer 7 and analyzed. The laptop 7 automatically searches the pre-selected spectral databases and uses correlation software to determine the "best matches" within a specified confidence level if any exist. The result is automatically transmitted to the operator. The spectral fingerprint(s) of the test subject is automatically saved and catalogued.

FIG. 4 depicts an exemplary embodiment 40 of a method for analyzing a subject.

At step 41, one or more optical probes are used for a subject that does not conform to a scanning surface.

At step 42, a presence of a subject to be scanned for on site automated material identification, documentation authenticity verification, or origin tracing is detected.

At step 43, one or more points on the subject are scanned, without necessarily repositioning the subject using a Raman scanner, upon detecting the presence of the subject on the scanner.

At step 44, emitted radiation is detected from the subject.

At step 45, a spectral signature of the emitted radiation from the subject is determined.

At step 46, the spectral signature of the emitted radiation from the subject is compared against one or more samples to determine if the spectral signature of the emitted radiation matches one of the one or more samples. This can be accomplished by, for example, correlating a Raman signature of the subject to spectra in a database and determining one or more best matches within a predetermined confidence level. If no matches are found within the predetermined confidence level a "No Match Found" response is generated.

At step 47, a "positive/negative" or a "best match" response, or a No Match Found response is forwarded to an operator.

At step 48, removal of the subject is detected and the spectral signature is automatically saved in memory and the system is reset for a next subject.

At step 51, one or more forms are used to accurately position the subject on a scanner surface.

At step 52, one or more optical probes are used for a subject that does not conform to a scanning surface.

At step 53, an adaptor is placed on the subject that conforms to the subject surface profile to ensure that no ambient light contaminates a subject spectral signature.

At step 54, erroneous spectral features are filter out of a sample signature.

At step 55, a presence of a subject to be scanned for on site automated material identification, documentation authenticity verification, or origin tracing is detected.

At step 56, a Raman spectrum is generated from one or more points on the subject.

At step 57, the spectral signature is transmitted over a communications link for analysis.

At step 58, the spectral signature of the emitted radiation from the subject is compared to one or more samples to determine if the spectral signature of the emitted radiation matches one of the one or more samples. This can be accomplished by, for example, correlating a Raman signature of the subject to spectra in a database and determining one or more best matches within a predetermined confidence level. If no matches are found within the predetermined confidence level a "No Match Found" response is generated. The one or more best matches or the "No Match Found" response is then forwarded to the operator.

Although various embodiments are specifically illustrated and described herein, it will be appreciated that modifications and variations of the invention are covered by the above teachings and are within the purview of the appended claims without departing from the spirit and intended scope of the invention. For example, certain applications of the Raman Scanner herein are discussed, but the invention is not limited to these applications as other applications would be apparent from review of this application. Furthermore, these examples should not be interpreted to limit the modifications and variations of the invention covered by the claims but are merely illustrative of possible variations.

What is claimed is:

1. An apparatus for performing on-site automatic nondestructive materials analysis on a subject using Raman spectroscopy comprising:
    a Raman scanner including:
        one or more laser light sources to illuminate the subject,
        a charge coupled device camera to capture emitted radiation from the subject, and
        an optical path to direct the emitted radiation from the subject to the charge coupled device camera;
    a database to store a plurality of spectral fingerprints of known samples; and
    a processor coupled to the scanner to compare a spectral signature in the emitted radiation from the subject to the plurality of spectral fingerprints of known samples in the database;
    an optical sensor coupled to the processor to detect a presence or absence of the subject;
    a memory, wherein upon said optical sensor automatically sensing removal of the subject, said processor saves a spectral signature from the subject in the memory and resets for a next subject.

2. The apparatus according to claim 1, wherein said processor generates a "positive/negative" or a "best match" response and forwards a result to an operator.

3. The apparatus according to claim 1, further comprising one or more optical probes for scanning a particular subject that does not conform to a scanning surface.

4. The apparatus according to claim 1, further comprising computer readable media having encoded thereon instructions that cause the processor to automate capture and correlation of a Raman signature of the subject to spectra in the database and determine a best match or matches within a predetermined confidence level, wherein if no matches are found within the predetermined confidence level a "No Match Found" response will be generated and forwarded to the operator.

5. The apparatus according to claim 1, further comprising computer readable media having stored thereon spectral correlation software to enable the processor to provide on site automated material identification.

6. The apparatus according to claim 1, further comprising computer readable media having stored thereon spectral correlation software to enable the processor to provide on site documentation authenticity verification.

7. The apparatus scanner according to claim 1, further comprising computer readable media having stored thereon spectral correlation software to enable the processor to provide capability to automatically trace a material to its origin using a database of known Raman signatures.

8. The apparatus scanner according to claim 1, further comprising moveable optics controlled by the processor to provide materials analysis of more than one point along the subject without physically moving the subject.

9. The apparatus according to claim 1, wherein said processor automatically generates Raman spectra of one or more points on the subject and correlates them to spectra in the database of known materials.

10. The apparatus according to claim 1, further comprising a communications device to transmit one or more results.

11. The apparatus according to claim 1, wherein the scanner includes a scanning surface and one or more optical probes having conjugated optics to enable scanning of a subject that does not conform to the scanner surface.

12. The apparatus according to claim 1, wherein the scanner includes a scanning surface and one or more forms for accurate positioning of the subject on the scanner surface.

13. The apparatus according to claim 1, wherein the scanner includes an adaptor that conforms to a subject surface profile to insure that no ambient light contaminates a subject spectral signature.

14. The apparatus according to claim 1, further comprising computer readable media having stored thereon software to enable the processor to filter out erroneous spectral features in a sample signature.

15. A method for analyzing a subject comprising:
    scanning the subject with a Raman scanner;
    detecting an emitted radiation from the subject;
    determining a spectral signature of the emitted radiation from the subject; and
    comparing the spectral signature of the emitted radiation from the subject against one or more samples to determine if the spectral signature of the emitted radiation matches one of the one or more samples; and
    detecting removal of the subject and automatically saving the spectral signature in memory and resetting for a next subject.

16. The method according to claim 15, further comprising generating a "positive/negative" or a "best match" response and forwarding a result to an operator.

17. The method according to claim 15, further comprising detecting a presence of the subject and automatically initiating said scanning upon detecting the presence of the subject.

18. The method according to claim 15, wherein said scanning includes scanning one or more points on the subject without physically repositioning the subject.

19. The method according to claim 15, wherein said scanning includes using one or more optical probes for scanning a particular subject that does not conform to a scanning surface.

20. The method according to claim 15, wherein said comparing includes correlating a Raman signature of the subject to spectra in a database and determining one or more best matches within a predetermined confidence level, if no matches are found within the predetermined confidence level generating a "No Match Found" response, and forwarding the one or more best matches or the "No Match Found" response to the operator.

21. The method according to claim 15, further comprising providing on site automated material identification.

22. The method according to claim 15, further comprising providing on site documentation authenticity verification.

23. The method according to claim 15, further comprising providing capability to automatically trace a material to its origin using a database of known Raman signatures.

24. A method for analyzing a subject comprising:
automatically generating a Raman spectra of one or more points on the subject; and
comparing the spectral signature of the emitted radiation from the subject against one or more samples to determine if the spectral signature of the emitted radiation matches one of the one or more samples; and
detecting removal of the subject and automatically saving the spectral signature in memory and resetting for a next subject.

25. The method according to claim 24, further comprising transmitting the spectral signature over a communications link for analysis.

26. The method according to claim 24, further comprising using one or more forms to accurately position the subject on a scanner surface.

27. The method according to claim 24, further comprising placing an adaptor on the subject that conforms to the subject surface profile to ensure that no ambient light contaminates a subject spectral signature.

28. The method according to claim 24, further comprising filtering out erroneous spectral features in a sample signature.

* * * * *